(12) United States Patent
McKenney et al.

(10) Patent No.: US 11,839,440 B2
(45) Date of Patent: Dec. 12, 2023

(54) ATTACHMENT FOR ROBOTIC MEDICAL SYSTEM

(71) Applicant: Corindus, Inc., Newton, MA (US)

(72) Inventors: Kyle McKenney, Westwood, MA (US); Eric Klem, Lexington, MA (US); Christopher O. Evans, Amherst, NH (US); Anthony Clegg Parker, New Ipswich, NH (US); Gordon Row, Groton, MA (US)

(73) Assignee: Corindus, Inc., Newton, MA (US)

( * ) Notice: Subject to any disclaimer, the term of this patent is extended or adjusted under 35 U.S.C. 154(b) by 0 days.

(21) Appl. No.: 17/813,138

(22) Filed: Jul. 18, 2022

(65) Prior Publication Data

US 2023/0036742 A1    Feb. 2, 2023

Related U.S. Application Data

(60) Provisional application No. 63/203,790, filed on Jul. 30, 2021.

(51) Int. Cl.
*A61B 34/30* (2016.01)
*A61B 90/50* (2016.01)
*F16B 21/00* (2006.01)

(52) U.S. Cl.
CPC .............. *A61B 34/30* (2016.02); *A61B 90/50* (2016.02); *F16B 21/00* (2013.01); *A61B 2034/301* (2016.02)

(58) Field of Classification Search
CPC ......... A61B 34/30; A61B 90/50; A61B 90/57; A61B 2017/00477; A61B 2034/301; A61B 2034/305; A61B 2034/306; A61B 2090/506; A61M 25/0113; A61M 25/09041; A61M 2025/0166; B25J 3/02; B25J 15/0408; B25J 15/045; B25J 15/0458; B25J 19/0041; F16B 3/00; F16B 7/02; F16B 9/05; F16B 9/052; F16B 9/09; F16B 21/00; F16B 21/02; F16B 21/09; Y10T 403/1616; Y10T 403/1624;
(Continued)

(56) References Cited

U.S. PATENT DOCUMENTS 548,182 A * 10/1895 Condict ................. A47B 57/50
403/254
2,816,770 A * 12/1957 De Vlieg .............. B23B 31/103
279/97

(Continued)

FOREIGN PATENT DOCUMENTS

DE       578974 C  *  6/1933
DE       3916315 A1 * 11/1990
(Continued)

OTHER PUBLICATIONS

European Search Report for Corresponding Application No. 22187437.3, dated Dec. 12, 2022.
(Continued)

*Primary Examiner* — Josh Skroupa

(57) ABSTRACT

A robotic medical system includes a post being substantially vertical and coupled to a base; a robotic drive having a socket for receiving the post; and at least one tapered interface shaped and oriented to engage the socket to prevent rotation of the robotic drive about at least one axis.

15 Claims, 10 Drawing Sheets

(58) Field of Classification Search
CPC ..... Y10T 403/32016; Y10T 403/32057; Y10T 403/32081; Y10T 403/32131; Y10T 403/32155; Y10T 403/39; Y10T 403/3906; Y10T 403/3913; Y10T 403/3933; Y10T 403/3973; Y10T 403/3981; Y10T 403/4694; Y10T 403/7016; Y10T 403/7037; Y10T 403/7039; Y10T 403/7041; Y10T 403/7045; Y10T 403/7073; Y10T 403/7098; Y10T 403/71; Y10T 403/7117

See application file for complete search history.

(56) References Cited

U.S. PATENT DOCUMENTS

| | | | | |
|---|---|---|---|---|
| 3,821,525 | A | 6/1974 | Eaton et al. | |
| 4,525,918 | A | 7/1985 | Puritz | |
| 4,697,947 | A * | 10/1987 | Bauer | F16L 37/148 403/14 |
| 4,770,073 | A * | 9/1988 | Palm | B25B 23/0035 403/361 |
| 5,312,338 | A | 5/1994 | Nelson et al. | |
| 5,350,101 | A | 9/1994 | Godlewski | |
| 5,582,489 | A * | 12/1996 | Marzio | F16D 1/02 403/325 |
| 5,893,300 | A * | 4/1999 | Liao | B62M 3/08 403/361 |
| 5,961,246 | A * | 10/1999 | Mitsubori | F16D 1/06 403/375 |
| 6,109,842 | A * | 8/2000 | Cook | B23B 27/002 279/158 |
| 6,478,028 | B1 | 11/2002 | Paolitto et al. | |
| 6,942,437 | B2 * | 9/2005 | Ripley | B23C 5/26 403/350 |
| 7,234,783 | B2 * | 6/2007 | MacKarvich | F16B 7/042 301/124.1 |
| 7,331,967 | B2 | 2/2008 | Lee et al. | |
| 7,766,856 | B2 | 8/2010 | Ferry et al. | |
| 7,766,894 | B2 | 8/2010 | Weitzner et al. | |
| 7,789,874 | B2 | 9/2010 | Yu et al. | |
| 7,972,298 | B2 | 7/2011 | Wallace et al. | |
| 8,052,636 | B2 | 11/2011 | Moll et al. | |
| 8,070,076 | B2 * | 12/2011 | Erickson | E03C 1/0404 239/587.5 |
| 8,092,397 | B2 | 1/2012 | Wallace et al. | |
| 8,298,633 | B1 * | 10/2012 | Chen | A47G 33/06 403/375 |
| 8,343,096 | B2 | 1/2013 | Kirschenman et al. | |
| 8,424,833 | B2 | 4/2013 | Mueller et al. | |
| 8,617,102 | B2 | 12/2013 | Moll et al. | |
| 8,684,952 | B2 | 4/2014 | Weitzner et al. | |
| 8,736,212 | B2 | 5/2014 | Sandhu et al. | |
| 8,777,230 | B2 * | 7/2014 | Ronald | B23B 31/1071 279/66 |
| 8,801,661 | B2 | 8/2014 | Moll et al. | |
| 9,283,046 | B2 | 3/2016 | Walker et al. | |
| 9,326,822 | B2 | 5/2016 | Lewis et al. | |
| 9,339,342 | B2 | 5/2016 | Prisco et al. | |
| 9,408,669 | B2 | 8/2016 | Kokish et al. | |
| 9,586,327 | B2 | 3/2017 | Schena | |
| 9,782,564 | B2 | 10/2017 | Zirps et al. | |
| 9,814,864 | B2 | 11/2017 | Scarpine et al. | |
| 9,820,817 | B2 | 11/2017 | Schlenk et al. | |
| 9,825,455 | B2 | 11/2017 | Sandhu et al. | |
| 10,047,908 | B1 * | 8/2018 | Bohle, II | B25J 15/0466 |
| 10,070,854 | B2 | 9/2018 | Duan et al. | |
| 10,213,264 | B2 | 2/2019 | Tanner et al. | |
| 10,307,214 | B2 | 6/2019 | Lathrop et al. | |
| 10,333,296 | B1 | 6/2019 | Wu et al. | |
| 10,335,957 | B2 | 7/2019 | Russell et al. | |
| 10,335,958 | B2 | 7/2019 | Kerestes et al. | |
| 10,485,623 | B2 | 11/2019 | Wiggers | |
| 10,493,575 | B2 * | 12/2019 | Hediger | B23B 31/1071 |
| 10,500,739 | B2 | 12/2019 | Auld et al. | |
| 10,631,871 | B2 | 4/2020 | Goldfarb et al. | |
| 10,646,229 | B2 | 5/2020 | Goldfarb et al. | |
| 10,653,427 | B2 | 5/2020 | Goldfarb et al. | |
| 10,661,449 | B2 * | 5/2020 | Zachary | B25J 15/0466 |
| 10,667,823 | B2 | 6/2020 | Goldfarb et al. | |
| 10,682,883 | B2 * | 6/2020 | Weis | B60B 27/00 |
| 10,694,647 | B2 * | 6/2020 | Yokoyama | B25J 15/0408 |
| 10,731,687 | B2 * | 8/2020 | Ponzer | F16B 7/18 |
| 10,813,535 | B2 | 10/2020 | Unai et al. | |
| 10,814,501 | B2 | 10/2020 | Auld et al. | |
| 10,821,046 | B2 | 11/2020 | Hares et al. | |
| 10,828,042 | B2 | 11/2020 | Goldfarb et al. | |
| 10,836,050 | B2 * | 11/2020 | Kalb | B25J 15/0416 |
| 10,856,948 | B2 | 12/2020 | Cagle et al. | |
| 10,893,941 | B2 | 1/2021 | Wei | |
| 10,944,261 | B2 | 3/2021 | Wu et al. | |
| 10,959,793 | B2 | 3/2021 | Devengenzo et al. | |
| 11,078,945 | B2 | 8/2021 | Grout et al. | |
| 11,141,229 | B2 * | 10/2021 | Sweeney, II | A61B 34/30 |
| 2002/0177789 | A1 | 11/2002 | Ferry et al. | |
| 2004/0254566 | A1 | 12/2004 | Plicchi et al. | |
| 2006/0237608 | A1 | 10/2006 | Hanson et al. | |
| 2007/0060879 | A1 | 3/2007 | Weitzner et al. | |
| 2007/0142971 | A1 | 6/2007 | Schena | |
| 2008/0214925 | A1 | 9/2008 | Wilson et al. | |
| 2008/0243064 | A1 | 10/2008 | Stahler et al. | |
| 2009/0082722 | A1 | 3/2009 | Munger et al. | |
| 2012/0071752 | A1 | 3/2012 | Sewell et al. | |
| 2014/0276389 | A1 | 9/2014 | Walker | |
| 2015/0142013 | A1 | 5/2015 | Tanner et al. | |
| 2017/0007343 | A1 | 1/2017 | Yu | |
| 2017/0348060 | A1 | 12/2017 | Blacker | |
| 2018/0104011 | A1 | 4/2018 | Kadokura et al. | |
| 2018/0228563 | A1 | 8/2018 | Smaby et al. | |
| 2018/0271604 | A1 * | 9/2018 | Grout | F16B 21/165 |
| 2019/0175887 | A1 | 6/2019 | Shameli | |
| 2019/0308312 | A1 | 10/2019 | Jackson et al. | |
| 2020/0078081 | A1 | 3/2020 | Jayme et al. | |
| 2020/0138529 | A1 | 5/2020 | Ragosta et al. | |
| 2020/0367979 | A1 | 11/2020 | Laakso et al. | |
| 2020/0368898 | A1 | 11/2020 | Perez | |
| 2021/0085300 | A1 | 3/2021 | Wang et al. | |
| 2021/0121051 | A1 | 4/2021 | Altshuler et al. | |
| 2021/0128262 | A1 | 5/2021 | Gomez et al. | |

FOREIGN PATENT DOCUMENTS

| | | | |
|---|---|---|---|
| DE | 10050528 | A1 * | 4/2002 |
| EP | 1970170 | | 9/2008 |
| EP | 2124800 | | 12/2009 |
| EP | 3590666 | A1 * | 1/2020 |
| GB | 2554876 | | 4/2018 |
| JP | 2015512666 | | 4/2015 |
| JP | 2016517331 | | 6/2016 |
| JP | 2020512076 | A * | 4/2020 |
| JP | 2020513945 | | 5/2020 |
| WO | 2018183212 | | 10/2018 |
| WO | WO-2019223843 | A1 * | 11/2019 |
| WO | 2021011518 | | 1/2021 |
| WO | 2021011533 | | 1/2021 |
| WO | 2021011551 | | 1/2021 |
| WO | 2021011554 | | 1/2021 |
| WO | 2022154975 | | 7/2022 |
| WO | 2022154976 | | 7/2022 |
| WO | 2022154977 | | 7/2022 |
| WO | 2022154978 | | 7/2022 |
| WO | 2022154980 | | 7/2022 |
| WO | 2015142785 | | 9/2022 |
| WO | 2022204211 | | 9/2022 |

OTHER PUBLICATIONS

Extended Search Report for Corresponding EP Application No. 22187437.3, dated Mar. 16, 2023.

* cited by examiner

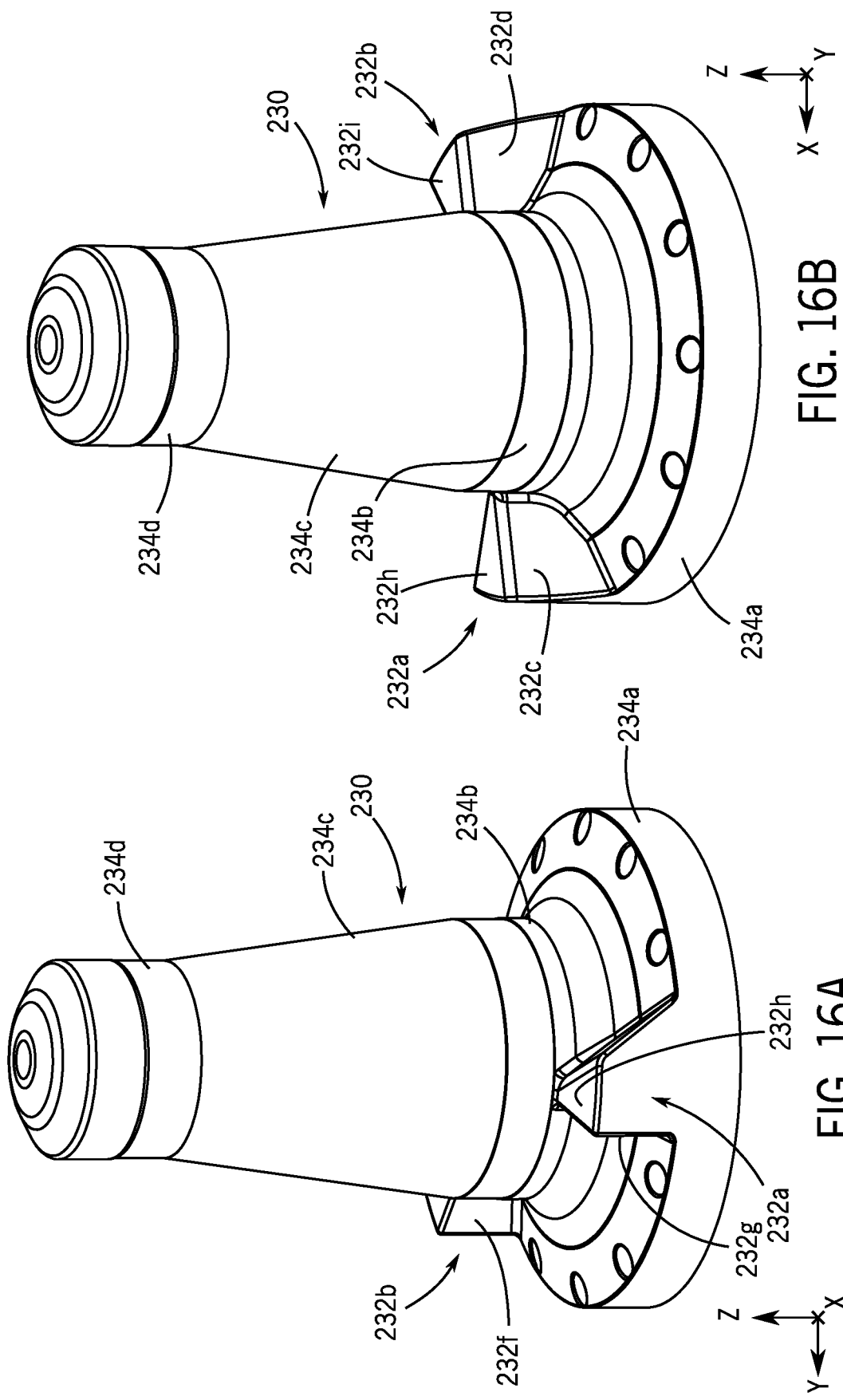

ATTACHMENT FOR ROBOTIC MEDICAL SYSTEM

CROSS-REFERENCE TO RELATED PATENT APPLICATIONS

This application claims benefit of U.S. Provisional Application No. 63/203,790 filed on Jul. 30, 2021, entitled ATTACHMENT FOR ROBOTIC MEDICAL SYSTEM, which is incorporated herein by reference in its entirety.

FIELD

The present invention relates generally to the field of robotic medical procedure systems and, in particular, to attachments for a robotic drive for such systems.

BACKGROUND

Catheters and other elongated medical devices (EMDs) may be used for minimally-invasive medical procedures for the diagnosis and treatment of diseases of various vascular systems, including neurovascular intervention (NVI) also known as neurointerventional surgery, percutaneous coronary intervention (PCI) and peripheral vascular intervention (PVI). These procedures typically involve navigating a guidewire through the vasculature, and via the guidewire advancing a catheter to deliver therapy. The catheterization procedure starts by gaining access into the appropriate vessel, such as an artery or vein, with an introducer sheath using standard percutaneous techniques. Through the introducer sheath, a sheath or guide catheter is then advanced over a diagnostic guidewire to a primary location such as an internal carotid artery for NVI, a coronary ostium for PCI, or a superficial femoral artery for PVI. A guidewire suitable for the vasculature is then navigated through the sheath or guide catheter to a target location in the vasculature. In certain situations, such as in tortuous anatomy, a support catheter or microcatheter is inserted over the guidewire to assist in navigating the guidewire. The physician or operator may use an imaging system (e.g., fluoroscope) to obtain a cine with a contrast injection and select a fixed frame for use as a roadmap to navigate the guidewire or catheter to the target location, for example, a lesion. Contrast-enhanced images are also obtained while the physician delivers the guidewire or catheter so that the physician can verify that the device is moving along the correct path to the target location. While observing the anatomy using fluoroscopy, the physician manipulates the proximal end of the guidewire or catheter to direct the distal tip into the appropriate vessels toward the lesion or target anatomical location and avoid advancing into side branches.

Robotic catheter-based procedure systems have been developed that may be used to aid a physician in performing catheterization procedures such as, for example, NVI, PCI and PVI. Examples of NVI procedures include coil embolization of aneurysms, liquid embolization of arteriovenous malformations and mechanical thrombectomy of large vessel occlusions in the setting of acute ischemic stroke. In an NVI procedure, the physician uses a robotic system to gain target lesion access by controlling the manipulation of a neurovascular guidewire and microcatheter to deliver the therapy to restore normal blood flow. Target access is enabled by the sheath or guide catheter but may also require an intermediate catheter for more distal territory or to provide adequate support for the microcatheter and guidewire. The distal tip of a guidewire is navigated into, or past, the lesion depending on the type of lesion and treatment. For treating aneurysms, the microcatheter is advanced into the lesion and the guidewire is removed and several embolization coils are deployed into the aneurysm through the microcatheter and used to block blood flow into the aneurysm. For treating arteriovenous malformations, a liquid embolic is injected into the malformation via a microcatheter. Mechanical thrombectomy to treat vessel occlusions can be achieved either through aspiration and/or use of a stent retriever. Depending on the location of the clot, aspiration is either done through an aspiration catheter, or through a microcatheter for smaller arteries. Once the aspiration catheter is at the lesion, negative pressure is applied to remove the clot through the catheter. Alternatively, the clot can be removed by deploying a stent retriever through the microcatheter. Once the clot has integrated into the stent retriever, the clot is retrieved by retracting the stent retriever and microcatheter (or intermediate catheter) into the guide catheter.

In PCI, the physician uses a robotic system to gain lesion access by manipulating a coronary guidewire to deliver the therapy and restore normal blood flow. The access is enabled by seating a guide catheter in a coronary ostium. The distal tip of the guidewire is navigated past the lesion and, for complex anatomies, a microcatheter may be used to provide adequate support for the guidewire. The blood flow is restored by delivering and deploying a stent or balloon at the lesion. The lesion may need preparation prior to stenting, by either delivering a balloon for pre-dilation of the lesion, or by performing atherectomy using, for example, a laser or rotational atherectomy catheter and a balloon over the guidewire. Diagnostic imaging and physiological measurements may be performed to determine appropriate therapy by using imaging catheters or fractional flow reserve (FFR) measurements.

In PVI, the physician uses a robotic system to deliver the therapy and restore blood flow with techniques similar to NVI. The distal tip of the guidewire is navigated past the lesion and a microcatheter may be used to provide adequate support for the guidewire for complex anatomies. The blood flow is restored by delivering and deploying a stent or balloon to the lesion. As with PCI, lesion preparation and diagnostic imaging may be used as well.

When support at the distal end of a catheter or guidewire is needed, for example, to navigate tortuous or calcified vasculature, to reach distal anatomical locations, or to cross hard lesions, an over-the-wire (OTW) catheter or coaxial system is used. An OTW catheter has a lumen for the guidewire that extends the full length of the catheter. This provides a relatively stable system because the guidewire is supported along the whole length. This system, however, has some disadvantages, including higher friction, and longer overall length compared to rapid-exchange catheters (see below). Typically to remove or exchange an OTW catheter while maintaining the position of the indwelling guidewire, the exposed length (outside of the patient) of guidewire must be longer than the OTW catheter. A 300 cm long guidewire is typically sufficient for this purpose and is often referred to as an exchange length guidewire. Due to the length of the guidewire, two operators are needed to remove or exchange an OTW catheter. This becomes even more challenging if a triple coaxial, known in the art as a tri-axial system, is used (quadruple coaxial catheters have also been known to be used). However, due to its stability, an OTW system is often used in NVI and PVI procedures. On the other hand, PCI procedures often use rapid exchange (or monorail) catheters. The guidewire lumen in a rapid exchange catheter runs only through a distal section of the catheter, called the monorail or rapid exchange (RX) section. With a RX system, the operator manipulates the interventional devices parallel to each other (as opposed to with an OTW system, in which the devices are manipulated in a serial configuration), and the exposed length of guidewire only needs to be slightly longer than the RX section of the catheter. A rapid exchange length guidewire is typically 180-200 cm long. Given the shorter length guidewire and monorail, RX catheters can be exchanged by a single operator. However, RX catheters are often inadequate when more distal support is needed.

SUMMARY

In accordance with one implementation a robotic medical system includes a post being substantially vertical and coupled to a base; a robotic drive having a socket for receiving the post; and at least one tapered interface shaped and oriented to engage the socket to prevent rotation of the robotic drive about at least one axis.

In one implementation the tapered interface includes at least two tapered keys.

In one implementation the post is substantially cylindrical, and the tapered keys are positioned about 180 degrees apart along a circumference of the post.

In one implementation the socket includes tapered cavities shaped and positioned to receive the tapered keys and cause physical engagement of the post and the robotic drive.

In one implementation the post includes at least one insertion interface to facilitate insertion of the post into the socket.

In one implementation the post is a cylinder, and the insertion interface includes at least one cylindrical portion along a length of the post, the cylindrical portion being configured to engage an internal bushing of the socket.

In one implementation the at least one cylindrical portion includes multiple cylindrical portions spaced along the length of the post.

In one implementation the multiple cylindrical portions have progressively smaller diameters along the length of the post.

In one implementation the insertion interface includes a convex tip at a termination of the post.

In one implementation each of the tapered keys extend from a conical portion of the post to an outer periphery of a base portion of the post.

In one implementation the post has a cross-sectional shape selected from one of circular, oval, or polygonal.

In one implementation the tapered keys comprise a sloped surface and a non-sloped surface, wherein the sloped surface is non-perpendicular to the base and the non-sloped surface is substantially perpendicular to the base.

In one implementation a robotic medical system comprises a positioning system coupled to a base, the positioning system including a substantially vertical post. T robotic drive has a socket for receiving the post. The post includes at least two tapered keys to engage the socket, the tapered keys positioned at a bottom end of the post and being oriented in an opposing manner to prevent rotation of the robotic drive about at least one axis.

In one implementation the socket includes tapered cavities for receiving the tapered keys to cause physical engagement of the post and the socket.

In one implementation the post includes at least one insertion interface to facilitate insertion of the post into the socket.

In one implementation the insertion interface includes at least one cylindrical portion along a length of the post, the cylindrical portion being configured to engage an internal bushing provided in the socket.

In one implementation the insertion interface includes a convex tip at a termination of the post.

In one implementation the tapered keys comprise a sloped surface and a non-sloped surface, wherein the sloped surface is non-perpendicular to the base and the non-sloped surface is substantially perpendicular to the base.

In one implementation a robotic medical system comprises a positioning system coupled to a base. The positioning system includes a substantially vertical post, the post includes a receptacle provided at a top portion of the post. A robotic drive has an attachment interface for engaging the receptacle of the post and the receptacle includes a tapered interface and the attachment interface includes a tapered hook configured to engage the tapered interface of the receptacle.

In one implementation the receptacle further comprises a tapered cavity provided orthogonally from the tapered interface, and wherein the attachment interface includes a tapered protrusion for insertion into the tapered cavity.

In one implementation the engagement of the tapered interface and the tapered hook prevent yaw movement of the robotic drive, and engagement of the tapered cavity and the tapered protrusion prevent pitch movement of the robotic drive.

BRIEF DESCRIPTION OF THE DRAWINGS

The invention will become more fully understood from the following detailed description, taken in conjunction with the accompanying drawings, wherein the reference numerals refer to like parts in which:

FIG. 16A is a post in one perspective view for mounting of an example robotic drive for attachment to an example positioning system in accordance with an embodiment;

FIG. 16B is the post of FIG. 16A in another perspective view; and.

DETAILED DESCRIPTION

Figure 1:
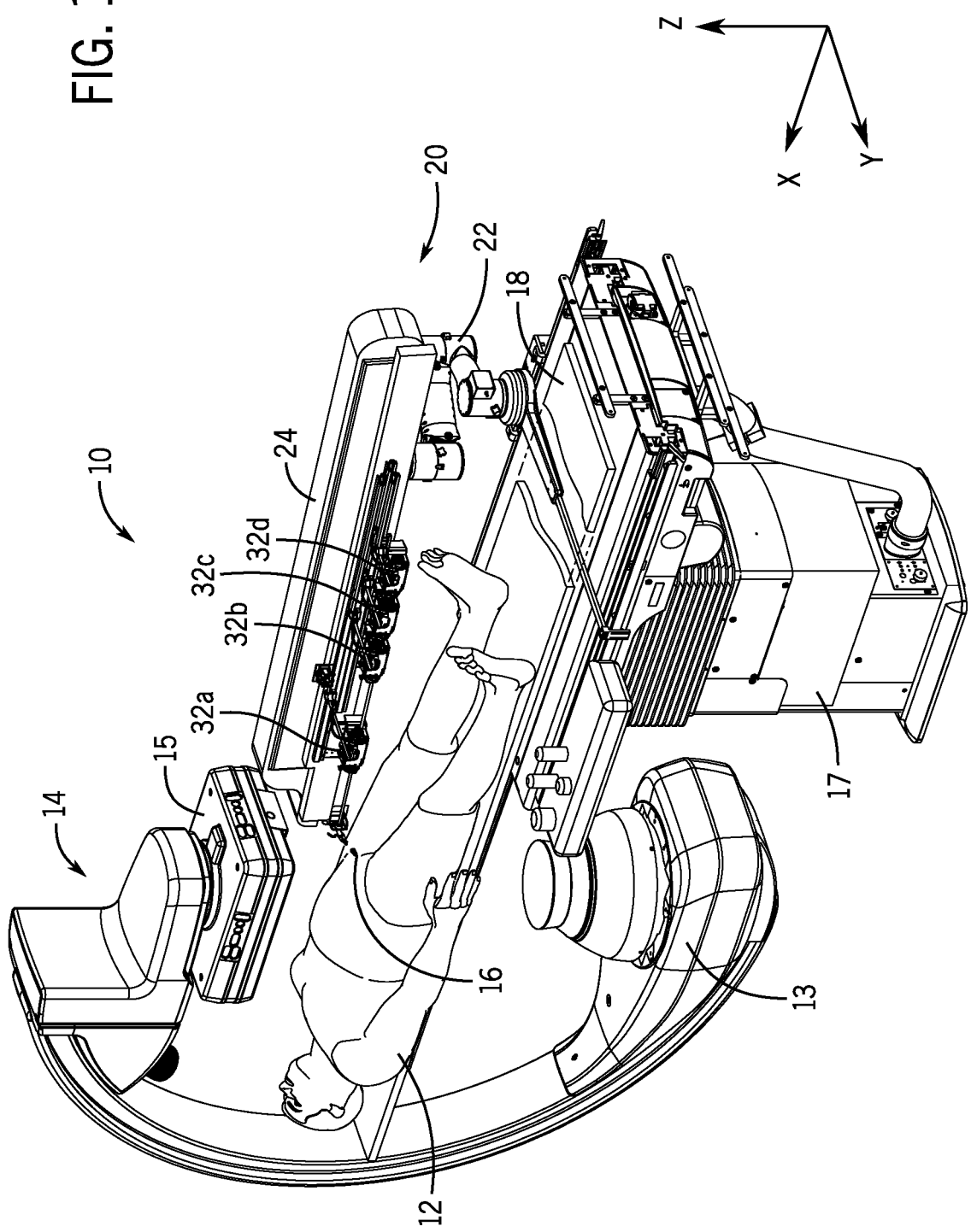
FIG. 1 is a perspective view of an example catheter-based procedure system in accordance with an embodiment.

FIG. 1 is a perspective view of an example catheter-based procedure system 10 in accordance with an embodiment. Catheter-based procedure system 10 may be used to perform catheter-based medical procedures, e.g., percutaneous intervention procedures such as a percutaneous coronary intervention (PCI) (e.g., to treat STEMI), a neurovascular interventional procedure (NVI) (e.g., to treat an emergent large vessel occlusion (ELVO)), peripheral vascular intervention procedures (PVI) (e.g., for critical limb ischemia (CLI), etc.). Catheter-based medical procedures may include diagnostic catheterization procedures during which one or more catheters or other elongated medical devices (EMDs) are used to aid in the diagnosis of a patient's disease. For example, during one embodiment of a catheter-based diagnostic procedure, a contrast media is injected onto one or more arteries through a catheter and an image of the patient's vasculature is taken. Catheter-based medical procedures may also include catheter-based therapeutic procedures (e.g., angioplasty, stent placement, treatment of peripheral vascular disease, clot removal, arterial venous malformation therapy, treatment of aneurysm, etc.) during which a catheter (or other EMD) is used to treat a disease. Therapeutic procedures may be enhanced by the inclusion of adjunct devices 54 (shown in FIG. 2) such as, for example, intravascular ultrasound (IVUS), optical coherence tomography (OCT), fractional flow reserve (FFR), etc. It should be noted, however, that one skilled in the art would recognize that certain specific percutaneous intervention devices or components (e.g., type of guidewire, type of catheter, etc.) may be selected based on the type of procedure that is to be performed. Catheter-based procedure system 10 can perform any number of catheter-based medical procedures with minor adjustments to accommodate the specific percutaneous intervention devices to be used in the procedure.

Catheter-based procedure system 10 includes, among other elements, a bedside unit 20 and a control station (not shown). Bedside unit 20 includes a robotic drive 24 and a positioning system 22 that are located adjacent to a patient 12. Patient 12 is supported on a patient table 18. The positioning system 22 is used to position and support the robotic drive 24. The positioning system 22 may be, for example, a robotic arm, an articulated arm, a holder, etc. The positioning system 22 may be attached at one end to, for example, the patient table 18 (as shown in FIG. 1), a base, or a cart. The other end of the positioning system 22 is attached to the robotic drive 24. The positioning system 22 may be moved out of the way (along with the robotic drive 24) to allow for the patient 12 to be placed on the patient table 18. Once the patient 12 is positioned on the patient table 18, the positioning system 22 may be used to situate or position the robotic drive 24 relative to the patient 12 for the procedure. In an embodiment, patient table 18 is operably supported by a pedestal 17, which is secured to the floor and/or earth. Patient table 18 is able to move with multiple degrees of freedom, for example, roll, pitch, and yaw, relative to the pedestal 17. Bedside unit 20 may also include controls and displays 46 (shown in FIG. 2). For example, controls and displays may be located on a housing of the robotic drive 24.

Generally, the robotic drive 24 may be equipped with the appropriate percutaneous interventional devices and accessories 48 (shown in FIG. 2) (e.g., guidewires, various types of catheters including balloon catheters, stent delivery systems, stent retrievers, embolization coils, liquid embolics, aspiration pumps, device to deliver contrast media, medicine, hemostasis valve adapters, syringes, stopcocks, inflation device, etc.) to allow a user or operator to perform a catheter-based medical procedure via a robotic system by operating various controls such as the controls and inputs located at the control station. Bedside unit 20, and in particular robotic drive 24, may include any number and/or combination of components to provide bedside unit 20 with the functionality described herein. The robotic drive 24 includes a plurality of device modules 32a-d mounted to a rail or linear member. Each of the device modules 32a-d may be used to drive an EMD such as a catheter or guidewire. For example, the robotic drive 24 may be used to automatically feed a guidewire into a diagnostic catheter and into a guide catheter in an artery of the patient 12. One or more devices, such as an EMD, enter the body (e.g., a vessel) of the patient 12 at an insertion point 16 via, for example, an introducer sheath.

Bedside unit 20 is in communication with the control station (not shown), allowing signals generated by the user inputs of the control station to be transmitted wirelessly or via hardwire to the bedside unit 20 to control various functions of bedside unit 20. As discussed below, control station 26 may include a control computing system 34 (shown in FIG. 2) or be coupled to the bedside unit 20 through the control computing system 34. Bedside unit 20 may also provide feedback signals (e.g., loads, speeds, operating conditions, warning signals, error codes, etc.) to the control station, control computing system 34 (shown in FIG. 2), or both. Communication between the control computing system 34 and various components of the catheter-based procedure system 10 may be provided via a communication link that may be a wireless connection, cable connections, or any other means capable of allowing communication to occur between components. The control station or other similar control system may be located either at a local site (e.g., local control station 38 shown in FIG. 2) or at a remote site (e.g., remote control station and computer system 42 shown in FIG. 2). Catheter procedure system 10 may be operated by a control station at the local site, a control station at a remote site, or both the local control station and the remote control station at the same time. At a local site, a user or operator and the control station are located in the same room or an adjacent room to the patient 12 and bedside unit 20. As used herein, a local site is the location of the bedside unit 20 and a patient 12 or subject (e.g., animal or cadaver) and the remote site is the location of a user or operator and a control station used to control the bedside unit 20 remotely. A control station (and a control computing system) at a remote site and the bedside unit 20 and/or a control computing system at a local site may be in communication using communication systems and services 36 (shown in FIG. 2), for example, through the Internet. In an embodiment, the remote site and the local (patient) site are away from one another, for example, in different rooms in the same building, different buildings in the same city, different cities, or other different locations where the remote site does not have physical access to the bedside unit 20 and/or patient 12 at the local site.

The control station generally includes one or more input modules 28 configured to receive user inputs to operate various components or systems of catheter-based procedure system 10. In the embodiment shown, control station allows the user or operator to control bedside unit 20 to perform a catheter-based medical procedure. For example, input modules 28 may be configured to cause bedside unit 20 to perform various tasks using percutaneous intervention devices (e.g., EMDs) interfaced with the robotic drive 24 (e.g., to advance, retract, or rotate a guidewire, advance, retract or rotate a catheter, inflate or deflate a balloon located on a catheter, position and/or deploy a stent, position and/or deploy a stent retriever, position and/or deploy a coil, inject contrast media into a catheter, inject liquid embolics into a catheter, inject medicine or saline into a catheter, aspirate on a catheter, or to perform any other function that may be performed as part of a catheter-based medical procedure). Robotic drive 24 includes various drive mechanisms to cause movement (e.g., axial and rotational movement) of the components of the bedside unit 20 including the percutaneous intervention devices.

In one embodiment, input modules 28 may include one or more touch screens, joysticks, scroll wheels, and/or buttons. In addition to input modules 28, the control station 26 may use additional user controls 44 (shown in FIG. 2) such as foot switches and microphones for voice commands, etc. Input modules 28 may be configured to advance, retract, or rotate various components and percutaneous intervention devices such as, for example, a guidewire, and one or more catheters or microcatheters. Buttons may include, for example, an emergency stop button, a multiplier button, device selection buttons and automated move buttons. When an emergency stop button is pushed, the power (e.g., electrical power) is shut off or removed to bedside unit 20. When in a speed control mode, a multiplier button acts to increase or decrease the speed at which the associated component is moved in response to a manipulation of input modules 28. When in a position control mode, a multiplier button changes the mapping between input distance and the output commanded distance. Device selection buttons allow the user or operator to select which of the percutaneous intervention devices loaded into the robotic drive 24 are controlled by input modules 28. Automated move buttons are used to enable algorithmic movements that the catheter-based procedure system 10 may perform on a percutaneous intervention device without direct command from the user or operator 11. In one embodiment, input modules 28 may include one or more controls or icons (not shown) displayed on a touch screen (that may or may not be part of a display), that, when activated, causes operation of a component of the catheter-based procedure system 10. Input modules 28 may also include a balloon or stent control that is configured to inflate or deflate a balloon and/or deploy a stent. Each of the input modules 28 may include one or more buttons, scroll wheels, joysticks, touch screen, etc. that may be used to control the particular component or components to which the control is dedicated. In addition, one or more touch screens may display one or more icons (not shown) related to various portions of input modules 28 or to various components of catheter-based procedure system 10.

Catheter-based procedure system 10 also includes an imaging system 14. Imaging system 14 may be any medical imaging system that may be used in conjunction with a catheter based medical procedure (e.g., non-digital X-ray, digital X-ray, CT, MRI, ultrasound, etc.). In an exemplary embodiment, imaging system 14 is a digital X-ray imaging device that is in communication with the control station. In one embodiment, imaging system 14 may include a C-arm (shown in FIG. 1) that allows imaging system 14 to partially or completely rotate around patient 12 in order to obtain images at different angular positions relative to patient 12 (e.g., sagittal views, caudal views, anterior-posterior views, etc.). In one embodiment imaging system 14 is a fluoroscopy system including a C-arm having an X-ray source 13 and a detector 15, also known as an image intensifier.

Imaging system 14 may be configured to take X-ray images of the appropriate area of patient 12 during a procedure. For example, imaging system 14 may be configured to take one or more X-ray images of the head to diagnose a neurovascular condition. Imaging system 14 may also be configured to take one or more X-ray images (e.g., real time images) during a catheter-based medical procedure to assist the user or operator 11 of control station 26 to properly position a guidewire, guide catheter, microcatheter, stent retriever, coil, stent, balloon, etc. during the procedure. The image or images may be displayed on display 30. For example, images may be displayed on a display to allow the user or operator to accurately move a guide catheter or guidewire into the proper position.

In order to clarify directions, a rectangular coordinate system is introduced with X, Y, and Z axes. The positive X axis is oriented in a longitudinal (axial) distal direction, that is, in the direction from the proximal end to the distal end, stated another way from the proximal to distal direction. The Y and Z axes are in a transverse plane to the X axis, with the positive Z axis oriented up, that is, in the direction opposite of gravity, and the Y axis is automatically determined by right-hand rule.

Figure 2:
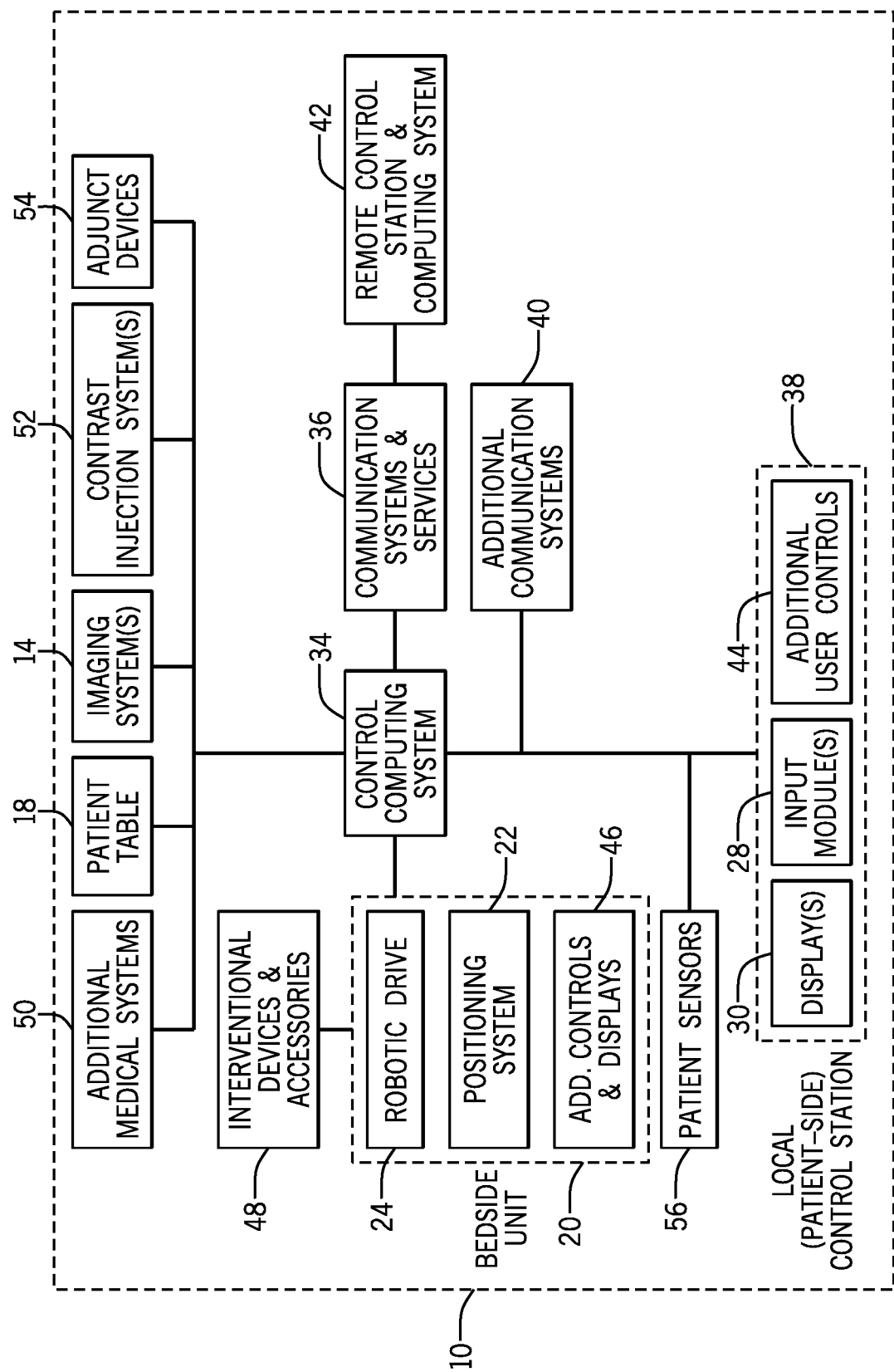
FIG. 2 is a schematic block diagram of an exemplary catheter-based procedure system in accordance with an embodiment.

FIG. 2 is a block diagram of catheter-based procedure system 10 in accordance with an example embodiment. Catheter-procedure system 10 may include a control computing system 34. Control computing system 34 may physically be, for example, part of a control station. Control computing system 34 may generally be an electronic control unit suitable to provide catheter-based procedure system 10 with the various functionalities described herein. For example, control computing system 34 may be an embedded system, a dedicated circuit, a general-purpose system programmed with the functionality described herein, etc. Control computing system 34 is in communication with bedside unit 20, communications systems and services 36 (e.g., Internet, firewalls, cloud services, session managers, a hospital network, etc.), a local control station 38, additional communications systems 40 (e.g., a telepresence system), a remote control station and computing system 42, and patient sensors 56 (e.g., electrocardiogram (ECG) devices, electroencephalogram (EEG) devices, blood pressure monitors, temperature monitors, heart rate monitors, respiratory monitors, etc.). The control computing system is also in communication with imaging system 14, patient table 18, additional medical systems 50, contrast injection systems 52 and adjunct devices 54 (e.g., IVUS, OCT, FFR, etc.). The bedside unit 20 includes a robotic drive 24, a positioning system 22 and may include additional controls and displays 46. As mentioned above, the additional controls and displays may be located on a housing of the robotic drive 24. Interventional devices and accessories 48 (e.g., guidewires, catheters, etc.) interface to the bedside system 20. In an embodiment, interventional devices and accessories 48 may include specialized devices (e.g., IVUS catheter, OCT catheter, FFR wire, diagnostic catheter for contrast, etc.) which interface to their respective adjunct devices 54, namely, an IVUS system, an OCT system, and FFR system, etc.

In various embodiments, control computing system 34 is configured to generate control signals based on the user's interaction with input modules 28 (e.g., of a control station such as a local control station 38 or a remote control station 42) and/or based on information accessible to control computing system 34 such that a medical procedure may be performed using catheter-based procedure system 10. The local control station 38 includes one or more displays 30, one or more input modules 28, and additional user controls 44. The remote control station and computing system 42 may include similar components to the local control station 38. The remote 42 and local 38 control stations can be different and tailored based on their required functionalities. The additional user controls 44 may include, for example, one or more foot input controls. The foot input control may be configured to allow the user to select functions of the imaging system 14 such as turning on and off the X-ray and scrolling through different stored images. In another embodiment, a foot input device may be configured to allow the user to select which devices are mapped to scroll wheels included in input modules 28. Additional communication systems 40 (e.g., audio conference, video conference, telepresence, etc.) may be employed to help the operator interact with the patient, medical staff (e.g., angio-suite staff), and/or equipment in the vicinity of the bedside.

Catheter-based procedure system 10 may be connected or configured to include any other systems and/or devices not explicitly shown. For example, catheter-based procedure system 10 may include image processing engines, data storage and archive systems, automatic balloon and/or stent inflation systems, medicine injection systems, medicine tracking and/or logging systems, user logs, encryption systems, systems to restrict access or use of catheter-based procedure system 10, etc.

As mentioned, control computing system 34 is in communication with bedside unit 20 which includes a robotic drive 24, a positioning system 22 and may include additional controls and displays 46, and may provide control signals to the bedside unit 20 to control the operation of the motors and drive mechanisms used to drive the percutaneous intervention devices (e.g., guidewire, catheter, etc.). The various drive mechanisms may be provided as part of a robotic drive 24.

Figure 3:
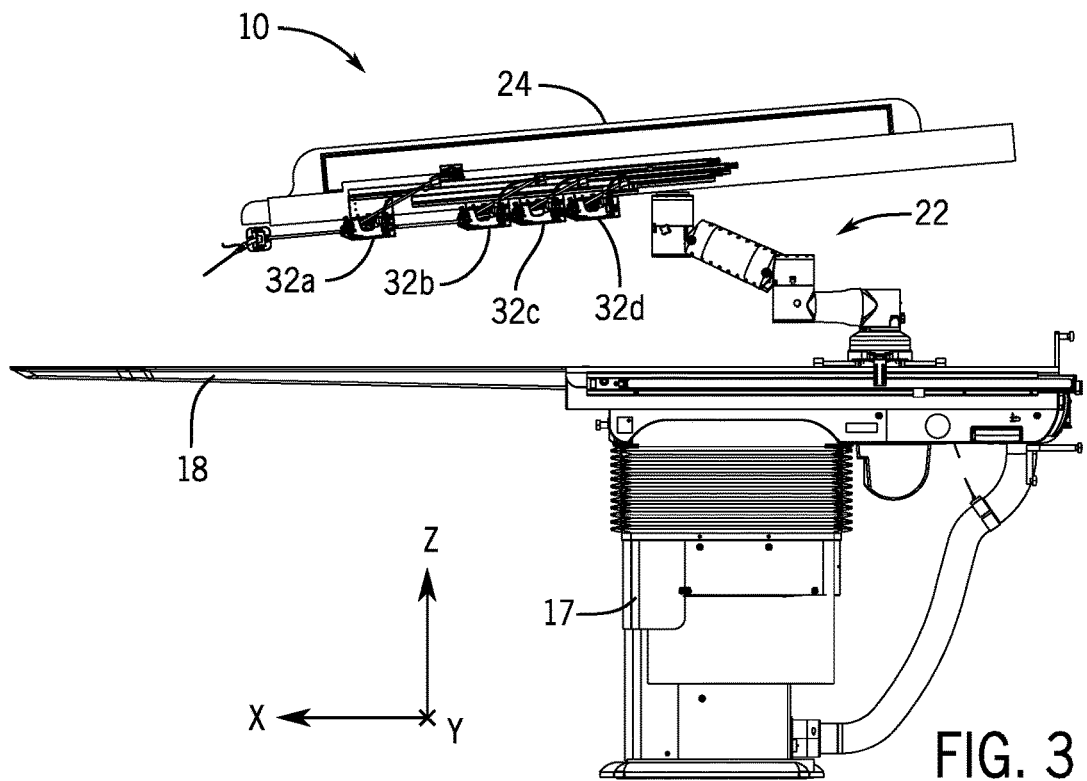
FIG. 3 is a side view of example catheter-based procedure system of FIG. 1 with certain components removed for clarity.

Referring now to FIG. 3, a side view of the example catheter-based procedure system 10 of FIG. 1 is illustrated with certain components (e.g., patient, C-arm) removed for clarity. As described above with reference to FIG. 1, the patient table 18 is supported on the pedestal 17, and the robotic drive 24 is mounted to the patient table with a positioning system 22. The positioning system 22 allows manipulation of the robotic drive 24 relative to the patient table 18. In this regard, the positioning system 22 is securely mounted to the patient table 18 and includes various joints and links/arms to allow the manipulation, as described below with reference to FIG. 4.

Figure 4:
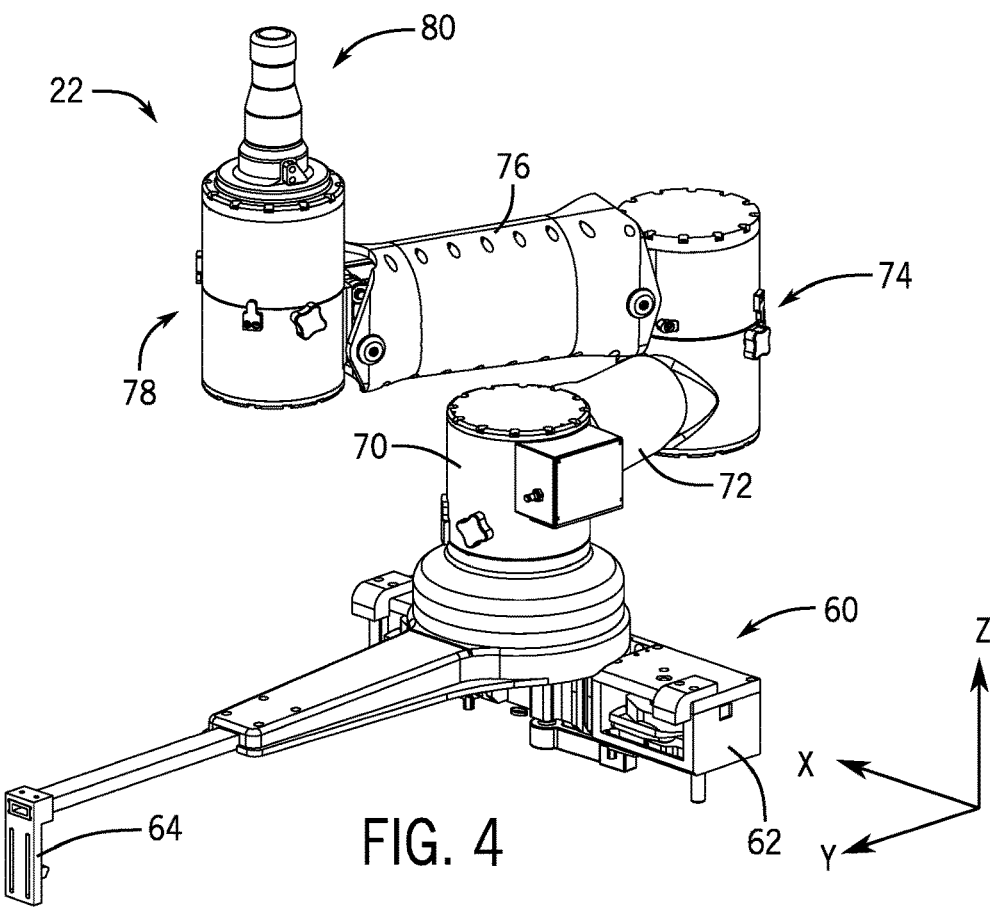
FIG. 4 is a perspective view of an example positioning system for a robotic drive in accordance with an embodiment.

FIG. 4 is a perspective view of an example positioning system 22 for a robotic drive in accordance with an embodiment. The positioning system 22 includes a mounting arrangement 60 to securely mount the positioning system 22 to the patient table 18. The mounting arrangement 60 includes an engagement mechanism to engage a first engagement member with a first longitudinal rail and a second engagement member with a second longitudinal rail of the patient table 18 to removably secure the positioning system to the patient table 18.

The positioning system 22 includes various segments and joints coupling to allow the robotic drive 24 to be positioned as desired, for example, relative to the patient. The positioning system 22 includes a first rotational joint 70 coupled to the mounting arrangement 60. The first rotational joint 70 allows rotation of a first arm 72, or link, about a rotational axis. In the illustrated example, the mounting arrangement 60 is in a substantially horizontal plane (e.g., the plane of the patient table 18), and the rotational axis is substantially vertical and runs through the center of the first rotational joint 70. The first rotational joint 70 can include circuitry to allow a user to control the rotation of the first rotational joint 70.

In the illustrated example, the first arm 72 is substantially horizontal with a first end coupled to the first rotational joint 70. The second end of the first arm 72 is coupled to a second rotational joint 74. In addition, the second rotational joint 74 is also coupled to a first end of a second arm 76. Thus, the second rotational joint 74 allows rotation of the second arm 76 relative to the first arm 72. As with the first rotational joint 70, the second rotational joint 74 allows rotation about a substantially vertical axis running through the center of the second rotational joint 74. Further, the second rotational joint 74 can include circuitry to allow a user to control the rotation of the second rotational joint 74.

In the illustrated example, a second end of the second arm 76 is coupled to a third rotational joint 78. The third rotational joint 78 includes a post 80 to allow mounting of the robotic drive 24 to the positioning system 22. Thus, the third rotational joint 78 allows rotation of the robotic drive 24 relative to the second arm 76. The third rotational joint 78 allows rotation about a substantially vertical axis running through the center of the third rotational joint 78. Further, the third rotational joint 78 can include circuitry to allow a user to control the rotation of the third rotational joint 78.

In one example, the second arm 76 includes a 4-arm linkage which can allow limited vertical movement of third rotational joint 78 relative to the second rotational joint 74. In this regard, the 4-arm linkage can allow vertical movement of the third rotational join 78, while maintaining the substantially vertical orientation of the third rotational joint 78 and the post 80.

Figure 5:
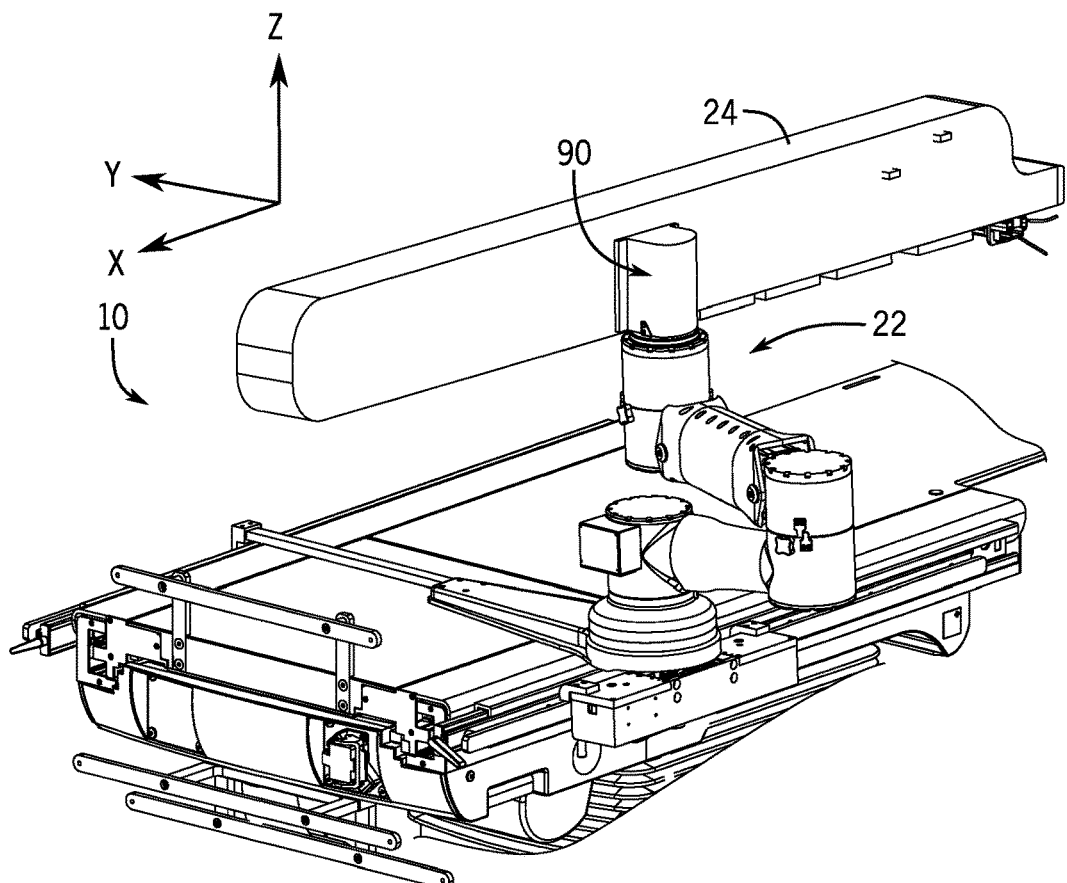
FIG. 5 is a perspective view of an example catheter-based procedure system with a robotic drive attached to a positioning system.

FIG. 5 is a perspective view of the catheter-based procedure system 10 with the robotic drive 24 attached to the positioning system 22. In various examples, the robotic drive 24 is mounted onto the positioning system 22 in a secure manner and without the use of any specific or specialized tools. Further, connection of the robotic drive 24 to the positioning system 22 is desired to be stiff with minimal or no backlash. In this regard, stiffness of the connection is desired in all six degrees of freedom. The six degrees of freedom includes translation along or rotation about the three axes of the coordinate system illustrated in FIG. 5. The X-axis is aligned longitudinally with the length of the robotic drive, the Y-axis is a horizontal axis perpendicular to the X-axis, and the Z-axis is aligned vertically. As used herein, "roll" refers to rotation of the robotic drive 24 about the X-axis, "pitch" refers to rotation of the robotic drive 24 about the Y-axis, and "yaw" refers to rotation of the robotic drive 24 about the Z-axis.

Figure 6:
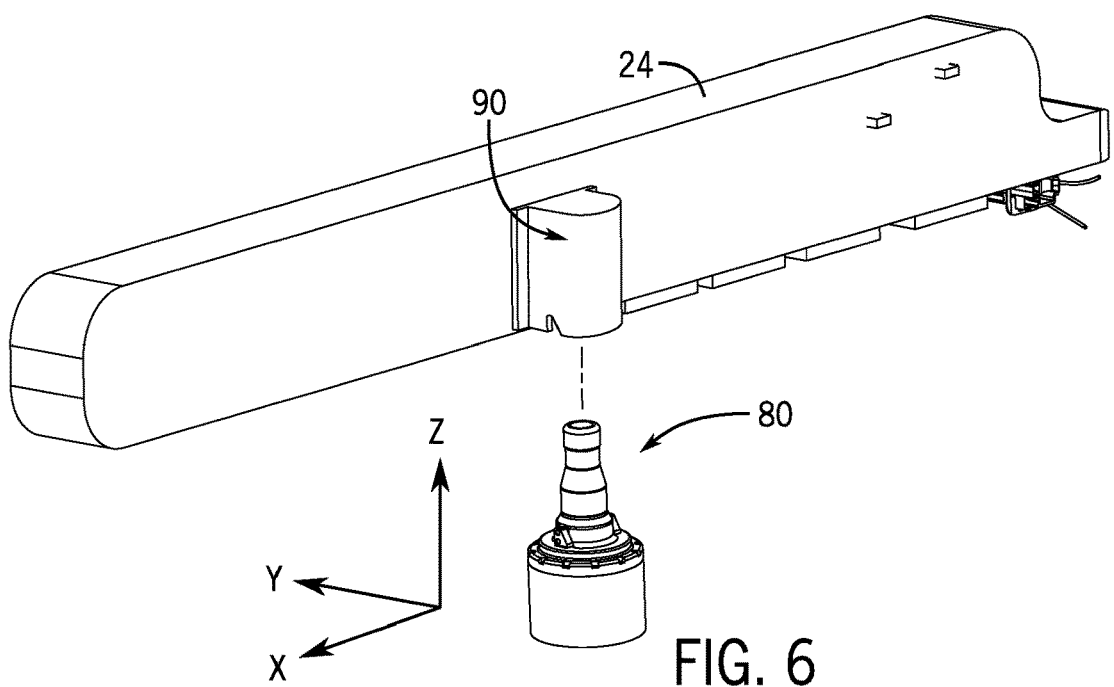
FIG. 6 is a perspective view illustrating an example post of a positioning system and an example robotic drive for attachment to the post in accordance with an embodiment.

In various examples described herein, the robotic drive is provided with a socket 90 for receiving the post 80 of the positioning system 22, as more clearly illustrated in FIG. 6. As noted above, the post 80 is substantially vertical and coupled to a base, such as the positioning system 22 or the patient table 18. Thus, in positioning of the robotic drive 24 onto the positioning system 22, the socket 90 of the robotic drive 24 receives the post 80 therein. The weight of the robotic drive 24 provides a sufficient downward force to secure the robotic drive 24 onto the positioning system 22 to prevent any translation in the vertical direction (i.e., along the Z-axis). The robotic drive may be equal to or about 222 N (or roughly 50 lbs.). The location of the post on the arm and the socket on the drive aids in keeping fluid out of the socket. However, it is also contemplated in one implementation that the post is located on robotic drive 24 and the socket is located on the arm.

Figure 7:
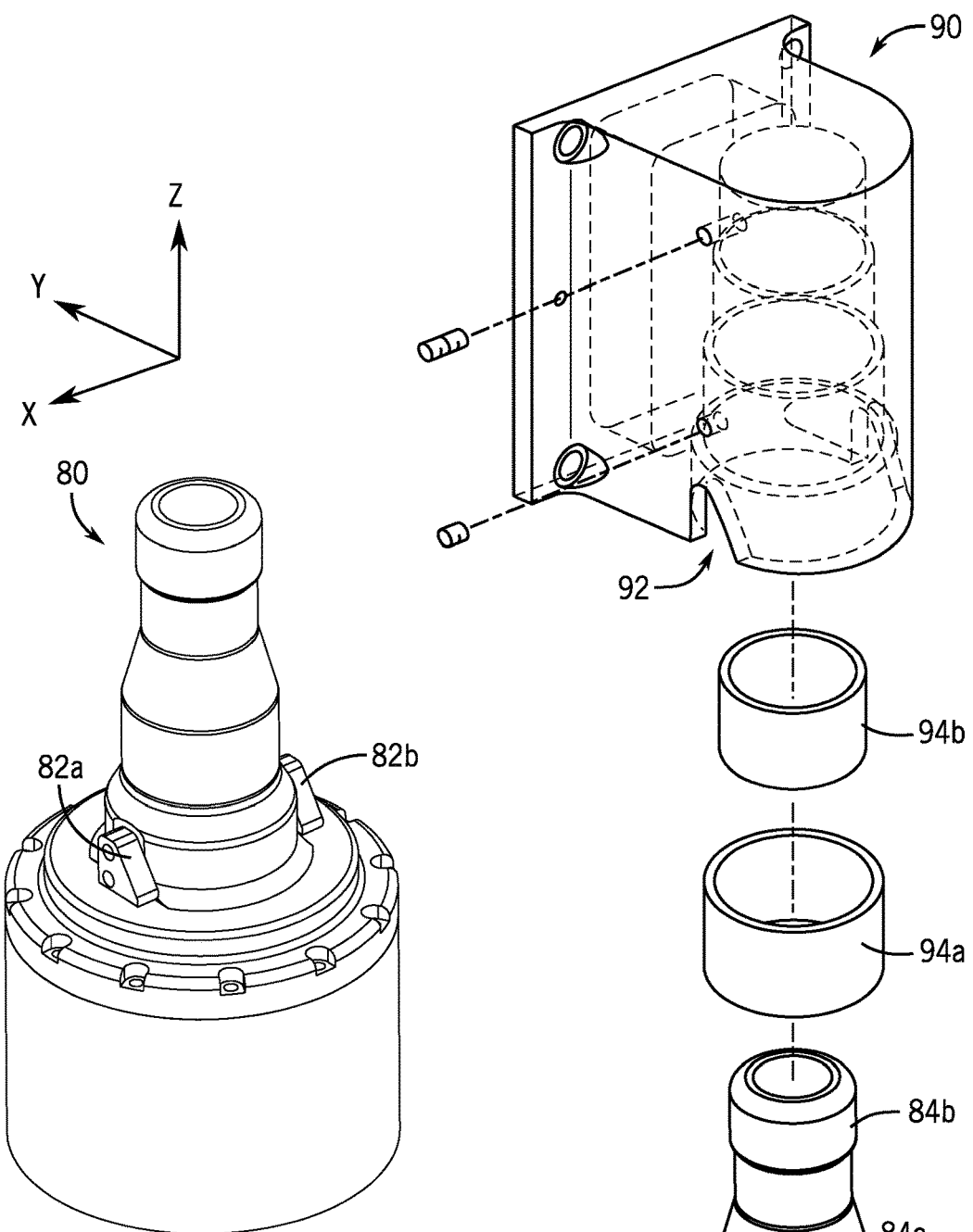
FIG. 7 is a detailed illustration of the example post of the positioning system for attachment of the robotic drive of FIG. 6.
Figure 8:
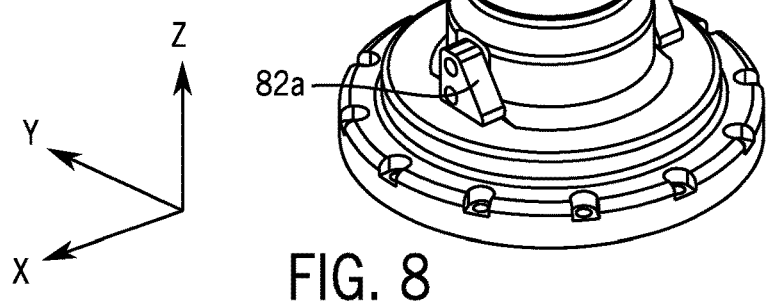
FIG. 8 is a detailed exploded view illustrating the attachment of the robotic drive to the positioning system FIGS. 6 and 7.

FIGS. 7 and 8 provide a detailed illustration of the example post 80 of the positioning system 22 and a detailed exploded view illustrating the attachment of the socket 90 of the robotic drive 24 to the socket 90 of the positioning system 22. In various examples, the post 80 is provided with at least one tapered interface to engage the socket 90. The tapered interface is oriented to prevent rotation of the robotic drive 24 about at least one axis. In addition, the tapered keys also constrain in the vertically (Z-axis). In the example illustrated in FIGS. 7 and 8, the post 80 is provided with a set of tapered interfaces or keys 82a, 82b to engage the socket 90 of the robotic drive 24. The post has a top end and a bottom end. The bottom end is adjacent the base and the top end opposes bottom end. The tapered keys 82a, 82b are positioned at the bottom end of the post 80 and are oriented in an opposing manner to prevent rotation of the robotic drive about at least one axis. In the illustrated example, the tapered keys 82a, 82b are positioned on opposite sides of the post 80, or about 180 degrees apart along the circumference of the post 80. In other examples, the tapered keys 82a, 82b may be positioned at positions other than about 180 degrees apart, but spaced sufficiently apart such that the tapering of the tapered keys 82a, 82b prevents rotation of the robotic drive. Referring to FIG. 7, FIG. 16A and FIG. 16B first tapered key 82a includes a sloped surface 232c and a non-sloped surface 232g and second tapered key 82b includes a sloped surface 232d and a non-sloped surface 232f. The sloped and non-sloped surfaces extend upward from the base along the length of the post. Keys may be attached to the base or the post. The sloped surfaces 232c and 232d have a slope that is non-perpendicular to a base portion or an upper surface of base portion 234a. The non-sloped surfaces are perpendicular or substantially perpendicular to the ground plane and/or a base portion or upper surface of base portion. Tapered keys 82 and 82b each have a height extending from an upper surface of the base in a direction parallel to the longitudinal axis of post 80. The height and width of tapered keys 82 and 82b are sufficient to resist a torque applied to socket 236 about the post vertical or longitudinal axis to ensure that socket 236 does not climb the slope surfaces 232c and 232d of the tapered keys 82 and 82b respectively. The geometry of tapered keys 82 and 82b can also be applied to post 80 and post 110 described herein. In the embodiment shown in FIG. 8, the tapered keys 82a, 82b have the same shape and are in the same orientation, 180 degrees apart from each other. Similarly, the corresponding tapered cavities 92 have the same shape and are in the same orientation, 180 degrees apart from each other, corresponding to the position of the tapered keys 82a, 82b. In the examples of FIGS. 7 and 8, the set of tapered keys 82a, 82b includes two keys. In other examples, the number of keys may be other than two. For example, additional tapered keys may be provided to increase the resistance against rotation of the robotic drive. In one implementation, a single key has two opposing tapered surfaces.

The taper angles of the tapered keys 82a, 82b are selected to prevent rotation of the robotic drive. In this regard, tapering of the tapered keys 82a, 82b should be sufficiently steep such that the weight of the robotic drive prevents the drive climbing up the steepness of the tapered keys 82a, 82b. On the other hand, the steepness of the tapering of the tapered keys 82a, 82b should be limited to allow installation and removal of the robotic drive without excessive resistance.

The socket 90 of the robotic drive 24 is provided with tapered cavities 92 for receiving the tapered keys 82a, 82b to cause physical engagement of the post and the robotic drive. In this regard, the tapered keys 82a, 82b of the post 80 and the corresponding tapered cavities 92 of the socket 90 are positioned to engage one another and to orient the robotic drive 24 in a desired orientation in the X-Y plane relative to the positioning system 22. In various examples, the tapered keys 82a, 82b are sized sufficiently large to at least allow the tapered surface of the cavities 92 to make secure contact with the tapered keys 82a, 82b.

Further, the tapered keys 82a, 82b of the post 80, as well as the corresponding cavities 92 of the socket 90, are formed as facing in the same direction and are, thus, rotationally opposed to one another. In this regard, the tapering of the tapered keys 82a, 82b in opposing rotational directions along the circumference of the post 80 prevents or minimizes rotation about the Z-axis, or yawing.

In the illustrated example of FIGS. 7 and 8, the post 80 includes at least one insertion interface to facilitate insertion of the post 80 into the socket 90. In this regard, the post 80 is provided with cylindrical portions 84a, 84b. The cylindrical portions 84a, 84b are formed along the vertical length of the post 80. In the example illustrated in FIGS. 7 and 8, the post 80 is provided with two cylindrical portions 84a, 84b that are spaced apart along the vertical length of the post 80

Correspondingly, the socket 90 is provided with internal bushings 94a, 94b that are positioned along the vertical length of the cavity of the socket 90. In the example of FIG. 8, the bushings are illustrated as separate bushings positioned into individual regions of the socket 90 to correspond to the position of the cylindrical portions 84a, 84b of the post 80. In other examples, the multiple bushings 94a, 94b may be formed as part of a single, integrated piece within the socket. The single, integrated piece may provide for a smoother surface with minimal discontinuities or ledges. When the post 80 is received in the socket 90, the cylindrical portions 84a, 84b engage corresponding bushings 94a, 94b. The bushings 94a, 94b are sized to securely fit around the cylindrical portions 84a, 84b, thus preventing any lateral movement within the X-Y plane of the robotic drive 24 relative to the positioning system 22. Further, the secure fit of the cylindrical portions 84a, 84b to the bushings 94a, 94b along the vertical length of the post 80 and the cavity of the socket 90 minimizes or prevents rotation of the robotic drive 24 relative to the positioning system 22 about the X-axis (roll) and the Y-axis (pitch).

To facilitate insertion of the post 80 into the socket 90, the cylindrical portions 84a, 84b have progressively smaller diameters along the length of the post. In this regard, the first cylindrical portion 84a from the bottom of the post has a larger diameter than the second cylindrical portion 84b. Thus, during insertion, the second cylindrical portion 84b passes through the bushing 94a corresponding to the first cylindrical portion 84a without resistance. The use of multiple cylindrical portions, with sufficient tolerances, provides stability and resistance against rotation about the X-axis (roll) and about the Y-axis (pitch).

Figure 9A:
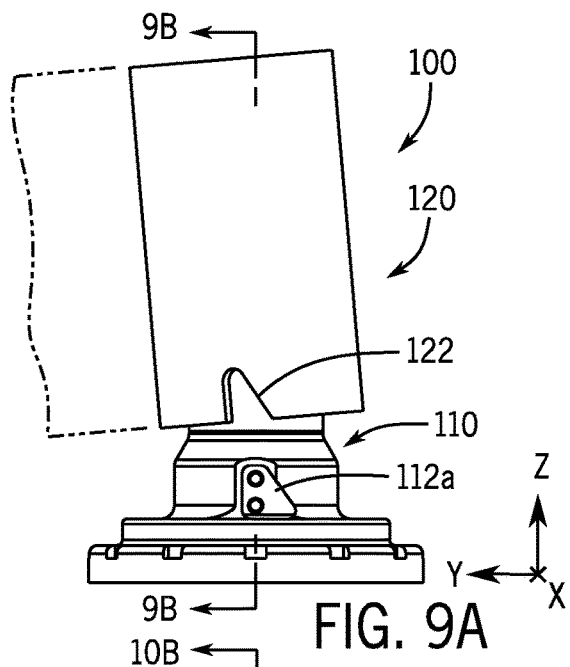
FIGS. 9A, 10A and 11A illustrate the mounting of an example robotic drive for attachment to an example positioning system in accordance with an embodiment.
Figure 9B:
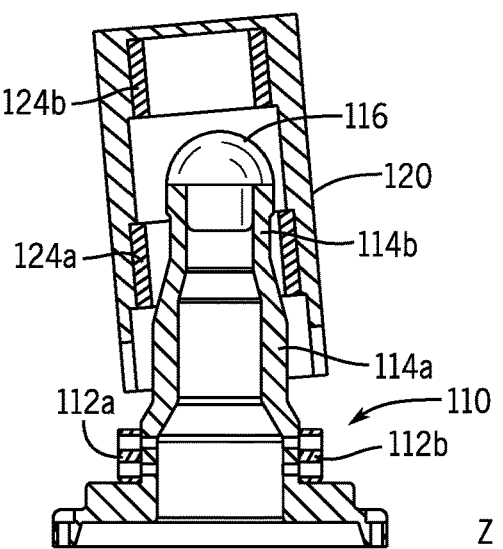
FIGS. 9B, 10B and 11B are cross-sectional views of FIGS. 9A, 10A and 11A, respectively.
Figure 10A:
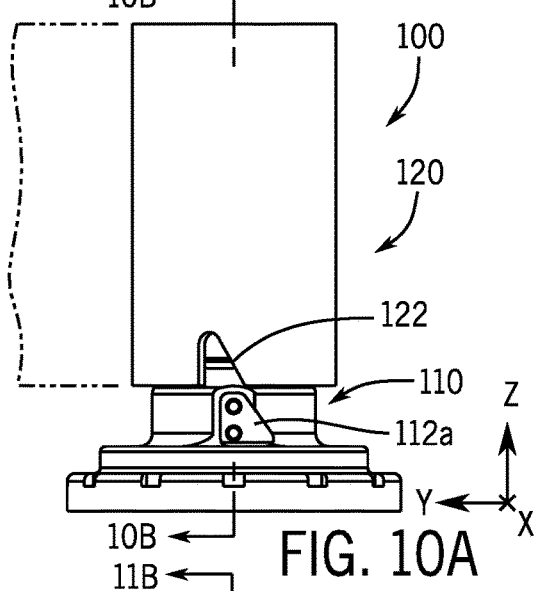
Figure 10B:
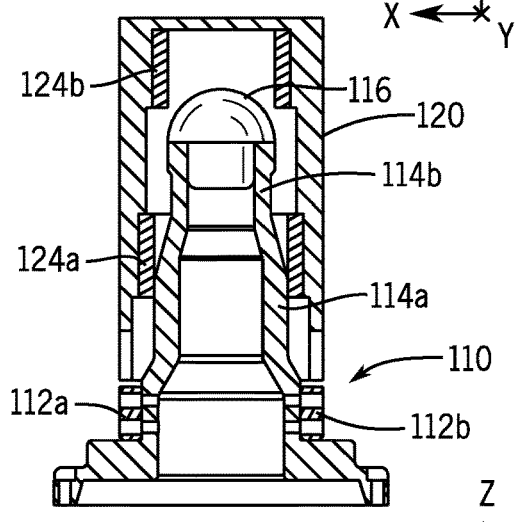
Figure 11A:
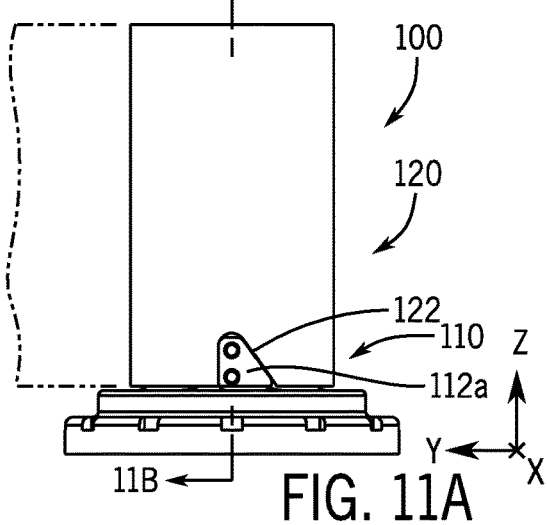
Figure 11B:
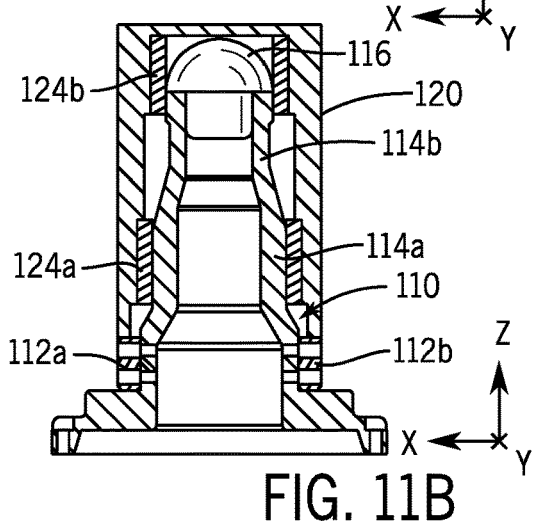

Various embodiments may include an electrical connection between the positioning system 22 and the robotic drive 24. In this embodiment, electrical pins and sockets would be integrated into the post 80 and mating socket 90, and as the mechanical connection is made, the electrical connection would be made simultaneously FIGS. 9A, 10A and 11A illustrate the mounting of an example robotic drive for attachment to an example positioning system in accordance with another embodiment, and FIGS. 9B, 10B and 11B are cross-sectional views of FIGS. 9A, 10A and 11A, respectively. FIGS. 9A-11B illustrate an attachment 100 of a post 110 of a positioning system being inserted into a socket 120 of a robotic drive. The post 110 and the socket 120 of FIGS. 9A-11B are similar to the post 80 and socket 90, respectively, described above with reference to FIGS. 5-8. In this regard, the post 110 is provided with tapered interfaces or keys 112a, 112b at the bottom of the post 110. As described above, the tapered keys 112a, 112b are positioned on opposite sides of the post (i.e., about 180 degrees apart) and are oriented in the same direction (i.e., rotationally opposite). The socket 120 is provided with cavities 122 to receive the tapered keys 112a, 112b therein. Engagement of the tapered keys 112a, 112b of the post 110 and the cavities 122 of the socket 120 minimizes or prevents rotation about the Z-axis (yawing) of the robotic drive relative to the positioning system.

Additionally, the post 110 is provided with cylindrical portions 114a, 114b. Correspondingly, the socket 120 is provided with bushings 124a, 124b that are positioned along the vertical length of the cavity of the socket 120. When the post 110 is received in the socket 120 as illustrated in FIG. 11B, the cylindrical portions 114a, 114b engage corresponding bushings 124a, 124b. Engagement of the cylindrical portions 114a, 114b with the bushings 124a, 124b prevents any lateral movement within the X-Y plane of the robotic drive relative to the positioning system. Further, the secure fit of the cylindrical portions 114a, 114b to the bushings 124a, 124b along the vertical length of the post 110 and the cavity of the socket 120 minimizes or prevents rotation of the robotic drive relative to the positioning system about the X-axis (roll) and the Y-axis (pitch).

In the example illustrated in FIGS. 9A-11B, the post 110 is provided with an insertion interface at the top end of the post 110 in the form of a convex tip 116, which may be located at or near the top end of post The convex tip 116 facilitates insertion of the post 110 into the cavity of the socket 120. As illustrated in FIG. 10A and FIG. 10B, the convex tip 116 can serve as a guide for the insertion of the post 110 into the socket 120. Additionally, the use of the convex tip 116 prevents the top of the post 110 from being caught on a feature of the socket 120, thus ensuring that the post 110 is inserted into the socket 120 to ensure engagement of the socket 120 and the post 110. In the example illustrated in FIGS. 9A-11B, the convex tip 116 is a spherical tip. In other examples, the convex tip 116 may have any of a variety of convex forms. The design of the post and socket such that when the post and socket are being joined, misalignment in the yaw direction can be adjusted by manually moving the post and socket relative to one another until the socket property sets on the post. This is accomplished by the flat portion on the bottom of the socket.

Figure 17:
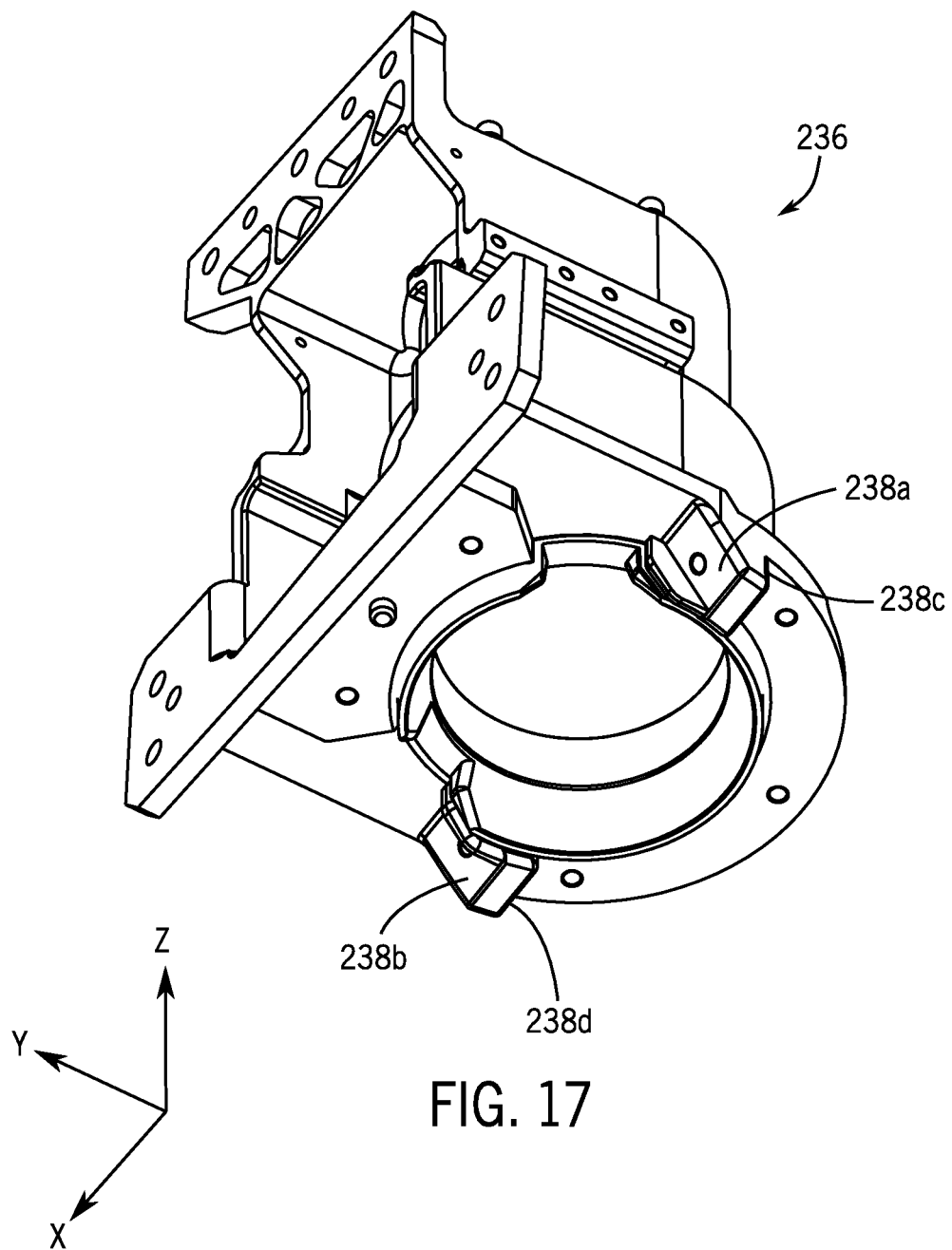
FIG. 17 is a socket that receives the post of FIG. 16A.

Referring to FIG. 16A, FIG. 16B and FIG. 17 another example attachment of a post of a base (e.g., positioning system) and a robotic drive 204 in accordance with an embodiment is illustrated. In one implementation a post 230 includes a cylindrical base portion 234a, a transition cylindrical portion 234b, a frusto conical portion 234c, and a top cylindrical portion 234d. In this implementation a first tapered interface or key 232a and a second tapered interface or key 232b are integrally formed with base portion 234a and extend the entire distance between an outer periphery of transition cylindrical portion 234b and an outer periphery of base portion 234a. Stated another way, the outer radial surfaces of tapered keys 232a and 232b respectively as measured from a longitudinal axis of post 230 is adjacent the outer radial periphery of base portion 234a. In one implementation tapered keys 232a and 232b are integrally formed with base portion 234a, transition cylindrical portion 234b, frusto conical portion 234c and top cylindrical portion 234d. In one implementation tapered keys 232a and 232b, base portion 234a, transition cylindrical portion 234b, frusto conical portion 234c and top cylindrical portion 234d have a hard black anodized surface.

First tapered key 232a includes a sloped surface 232c and substantially vertical surface 232g and second tapered key 232b includes a sloped surface 232d and a substantially vertical surface 232f. The sloped surfaces 232c and 232d have a slope that is non-perpendicular to an upper surface of base portion 234a. Tapered keys 232a and 232b each have a height extending from an upper surface of base portion 234a in a direction parallel to the longitudinal axis of post 230. Tapered key 232a includes an upper surface 232h and tapered key 232b includes an upper surface 232i. The height and width of tapered keys 232a and 232b are sufficient to resist a torque applied to socket 236 about the post vertical or longitudinal axis to ensure that socket 236 does not climb the slope surfaces 232c and 232d of the tapered keys 232a and 232b respectively. The geometry of tapered keys 232a and 232b can also be applied to post 80 and post 110 described herein. The cylindrical interfaces have an axial length that is short enough that a single interface can never react pitch or roll moments, they always must be reacted between 2 different cylindrical sections. If a single cylindrical interface could react these moments, the point loading would be very high and then it would be extremely difficult to load and remove the drive.

Referring to FIG. 17, socket 236 includes a cavity that receives post 230. Socket 236 includes a first key receiving portion 238a and a second key receiving portion 238b each having a sloped surface that aligns with the tapered key sloped surfaces 232c and 232d respectively in the installed position. First key receiving portion 238a and second key receiving portion 238b in one implementation is formed from a bronze material.

Figure 12:
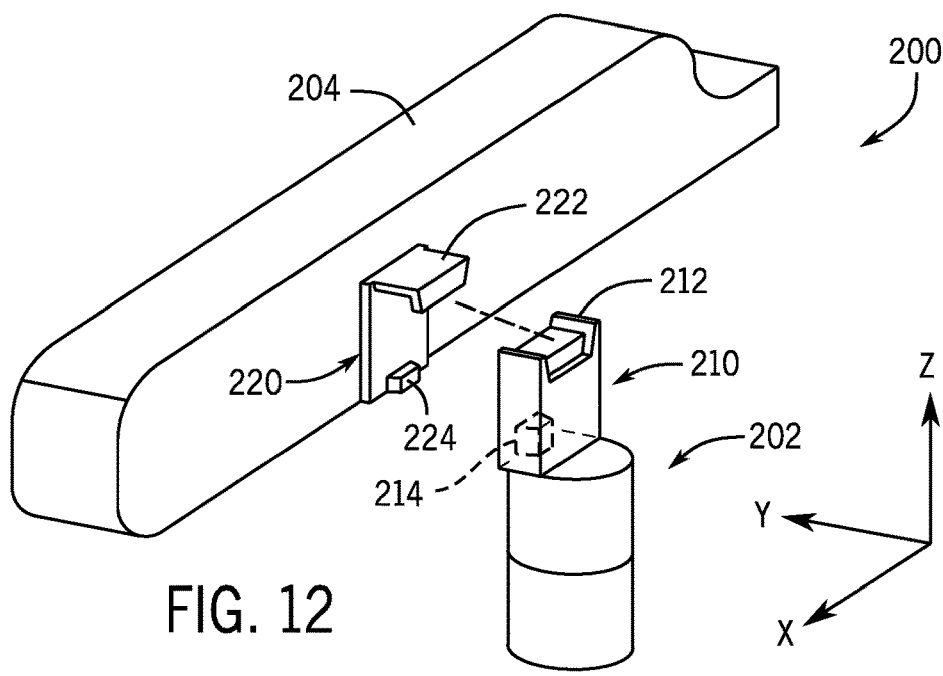
FIG. 12 is a perspective view illustrating an example post of a positioning system and an example robotic drive for attachment to the post in accordance with an embodiment.
Figure 13:
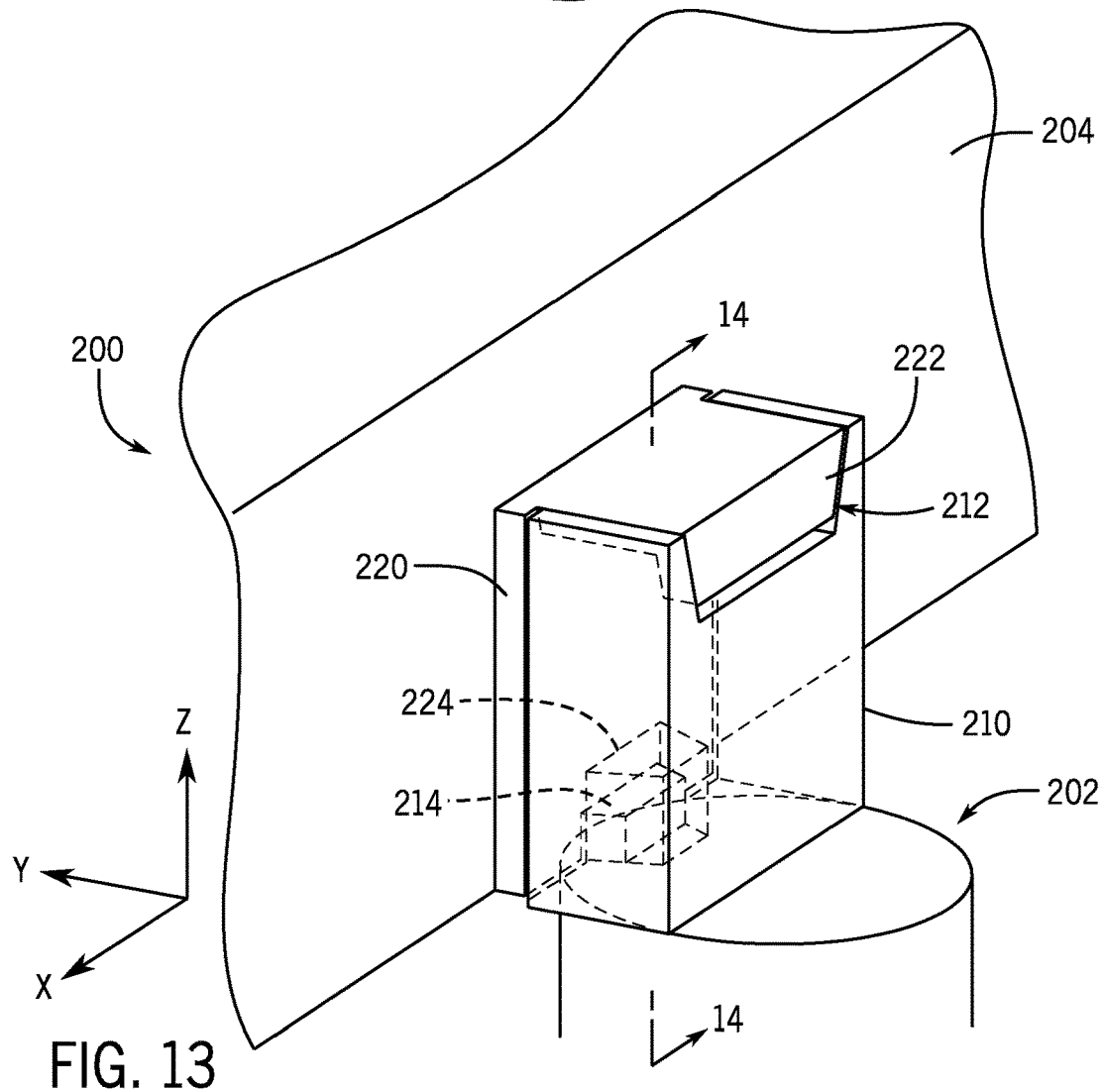
FIG. 13 is a detailed view illustrating the attachment of the robotic drive to the positioning system FIG. 12.
Figure 15:
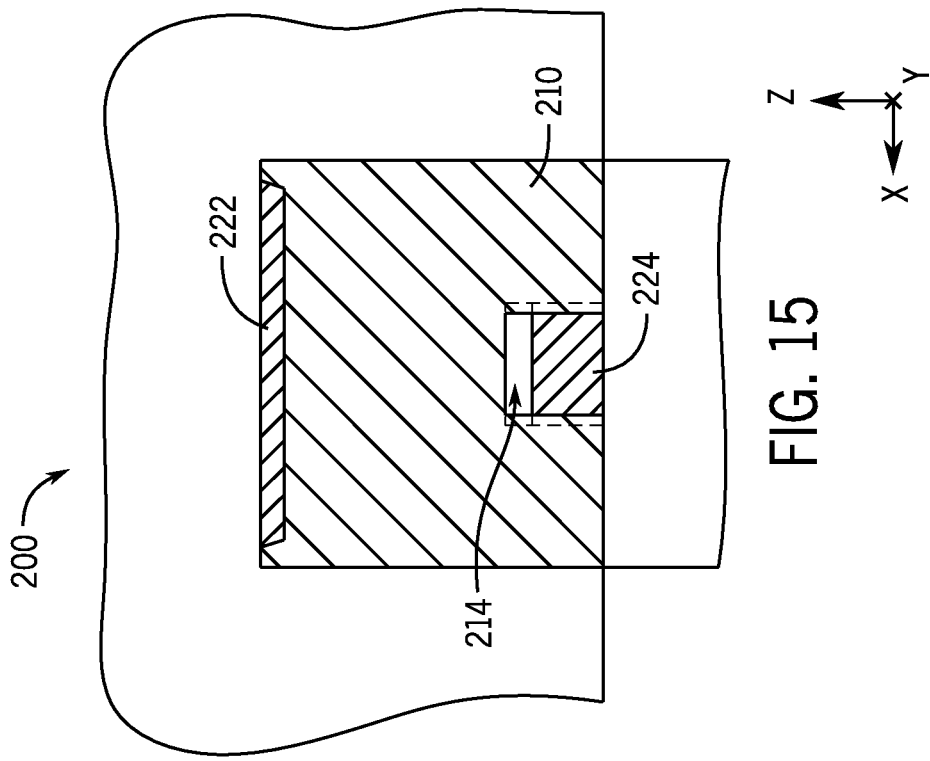
FIG. 15 is a cross-sectional view of the attachment of FIG. 13 and taken along 15-15 of FIG. 14.
Figure 14:
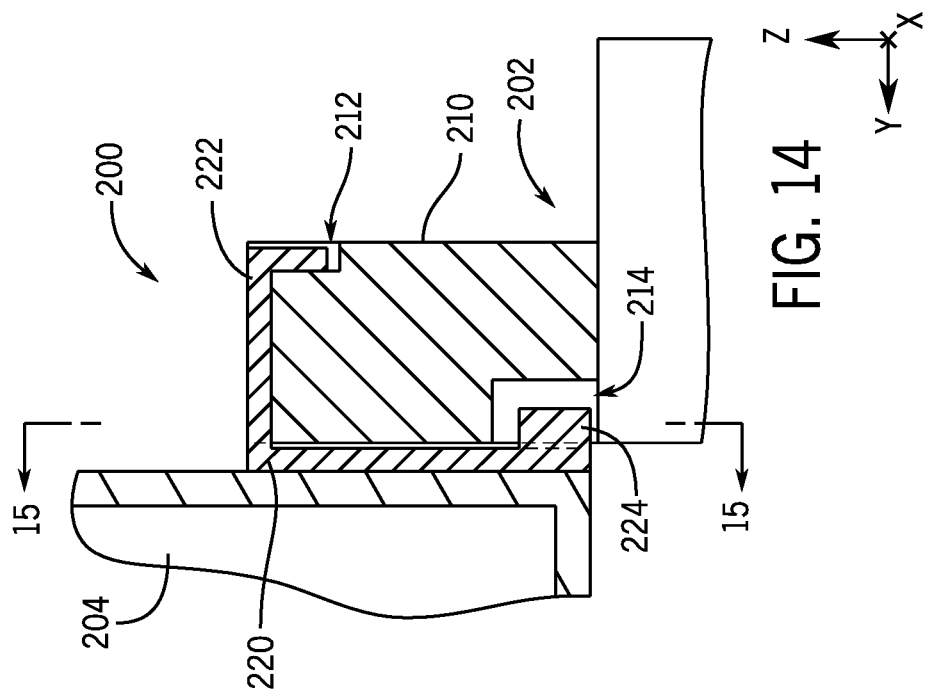
FIG. 14 is a cross-sectional view of the attachment of FIG. 13 taken along 14-14 of FIG. 13.

Referring now to FIGS. 12-15, another example attachment 200 of a post 202 of a base (e.g., positioning system) and a robotic drive 204 in accordance with an embodiment is illustrated. FIG. 12 is a perspective view illustrating the example post 202 and an example attachment interface 220 of the robotic drive 204 for attachment of the robotic drive 204 to the post 202. FIG. 13 illustrates the attachment 200 with the robotic drive 204 attached to the post 202.

The attachment interface 220 is formed as a socket for receiving at least a part of the substantially vertical post 202 therein. The post 202 is provided with a tapered interface 212 to engage the attachment interface 220. In this regard, the attachment interface 220 is provided with a tapered hook 222 to engage the tapered interface 212 of the post. The tapered interface 212 is oriented to prevent rotation of the robotic drive 204 about at least one axis.

The tapered hook 222 of the attachment interface 220 is formed at the top portion of the attachment interface 220.

The tapered interface 212 of the post 202 is formed in a receptacle 210 provided on the top surface of the post 202. As illustrated in FIG. 13, upon attachment of the robotic drive 204 to the post 202, the tapered hook 222 of the attachment interface 220 is positioned over and around the tapered interface 212 of the post 202, as more clearly illustrated in the cross-section view provided in FIG. 14.

The tapered interface 212 formed in the receptacle 210 is tapered downward. Thus, when the correspondingly tapered hook 222 is positioned onto the receptacle 210, the tapered surface of the tapered hook 222 engages the tapered surface of the tapered interface 212. This tapering engagement, with the downward force of the weight of the robotic drive, prevents vertical movement (along the Z-axis) of the robotic drive.

The receptacle 210 of the example post 202 further includes a tapered cavity 214 within the vertical plane of the receptacle 210. The tapered cavity 214 is formed on the side of the receptacle facing the robotic drive 204. Correspondingly, the attachment interface 220 of the robotic drive 204 is provided with a tapered protrusion 224 on a side surface of the attachment interface 220. The tapered protrusion 224 is formed on the side surface of the attachment interface 220 which faces the receptacle 210 and, therefore, is positioned for receipt by the tapered cavity 214 of the receptacle 210, as illustrated in FIG. 13 and the cross-section view of FIG. 15. The engagement of the tapered cavity 214 and the tapered protrusion 224 minimizes or prevents rotation of the robotic drive about the Y-axis (pitching).

The tapering of the tapered protrusion 224 and the tapered cavity 214 is orthogonal to the tapering of the tapered hook 222 and the tapered interface 212. In particular, while the tapered hook 222 and the tapered interface 212 are tapered downward in a vertical plane (the X-Z plane), the tapered protrusion 224 and the tapered cavity 214 are tapered in a horizontal plane (the X-Y plane). The engagement of the tapered protrusion 224 with the tapered cavity 214 minimizes or prevents rotation of the robotic drive about the Z-axis (yaw). The combination of the engagement of the hook 222 with the protrusion interface 212 and the engagement of the tapered protrusion 224 with the tapered cavity 214 minimizes or prevents rotation of the robotic drive 24 about the X-axis (roll). Thus, the combination of the engagement of the various tapered surfaces provides stiffness of the attachment in the desired six degrees of freedom. Note that the lower taper interface relies on the roll moment from the mass of the drive to keep it firmly engaged.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

We claim:

1. A robotic medical system, comprising:
   a post being substantially vertical and coupled to a base;
   a robotic drive having a socket for receiving the post; and
   a first tapered key integrated with the post and oriented to engage the socket, the first tapered key comprising a first substantially vertical surface and a first sloped surface opposing the first substantially vertical surface in a first rotational direction about a vertical axis of the post;
   a second tapered key integrated with the post and oriented to engage the socket, the second tapered key comprising a second substantially vertical surface and a second sloped surface opposing the second substantially vertical surface in a second rotational direction about the vertical axis of the post;
   wherein the first substantially vertical surface and the second substantially vertical surface resist rotation of the robotic drive about at least the vertical axis of the post when engaged with the socket.

2. The robotic medical system of claim 1, wherein the post is substantially cylindrical and the tapered keys are positioned about 180 degrees apart along a circumference of the post.

3. The robotic medical system of claim 1, wherein the socket includes tapered cavities shaped and positioned to receive the first tapered key and the second tapered keys and cause physical engagement of the post and the robotic drive.

4. The robotic medical system of claim 1, wherein the post includes at least one insertion interface to facilitate insertion of the post into the socket.

5. The robotic medical system of claim 4, wherein the post is a cylinder and the insertion interface includes at least one cylindrical portion along a length of the post, the cylindrical portion being configured to engage an internal bushing of the socket.

6. The robotic medical system of claim 5, wherein the at least one cylindrical portion includes multiple cylindrical portions spaced along the length of the post.

7. The robotic medical system of claim 6, wherein the multiple cylindrical portions have progressively smaller diameters along the length of the post.

8. The robotic medical system of claim 4, wherein the insertion interface includes a convex tip at a termination of the post.

9. The robotic medical system of claim 1, wherein each of the first tapered key and the second tapered key extend from a conical portion of the post to an outer periphery of a base portion of the post.

10. The robotic medical system of claim 1, wherein the post has a cross-sectional shape selected from one of circular, oval, or polygonal.

11. A robotic medical system, comprising:
    a positioning system coupled to a base, the positioning system including a substantially vertical post; and
    a robotic drive having a socket for receiving the post,
    wherein the post includes at least two tapered keys to engage the socket, each tapered key positioned at a bottom end of the post and comprising a substantially vertical surface and a sloped surface opposing the substantially vertical surface in a rotational direction about a vertical axis of the post, the substantially vertical surfaces being oriented in an opposing manner to resist rotation of the robotic drive about at least the vertical axis.

12. The robotic medical system of claim 11, wherein the socket includes tapered cavities for receiving the tapered keys to cause physical engagement of the post and the socket.

13. The robotic medical system of claim 11, wherein the post includes at least one insertion interface to facilitate insertion of the post into the socket.

14. The robotic medical system of claim 13, wherein the insertion interface includes at least one cylindrical portion along a length of the post, the cylindrical portion being configured to engage an internal bushing provided in the socket.

15. The robotic medical system of claim 13, wherein the insertion interface includes a convex tip at a termination of the post.

* * * * *